(12) United States Patent
Suttin et al.

(10) Patent No.: US 10,925,694 B2
(45) Date of Patent: *Feb. 23, 2021

(54) METHOD FOR SELECTING IMPLANT COMPONENTS

(71) Applicant: BIOMET 3I, LLC, Palm Beach Gardens, FL (US)

(72) Inventors: Zachary B. Suttin, West Palm Beach, FL (US); Bruce Berckmans, III, Palm Beach Gardens, FL (US); T. Tait Robb, Stewart, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,984

(22) Filed: Jul. 1, 2019

(65) Prior Publication Data

US 2019/0321139 A1  Oct. 24, 2019

Related U.S. Application Data

(63) Continuation of application No. 15/865,608, filed on Jan. 9, 2018, now Pat. No. 10,368,963, which is a
(Continued)

(51) Int. Cl.
*A61C 8/00* (2006.01)
*A61B 6/03* (2006.01)
(Continued)

(52) U.S. Cl.
CPC .......... *A61C 8/00* (2013.01); *A61B 6/032* (2013.01); *A61B 6/14* (2013.01); *A61B 6/505* (2013.01);
(Continued)

(58) Field of Classification Search
CPC . A61B 19/50; G06F 19/3437; G06F 17/5018; A61C 13/0004; A61C 2202/00; A61C 8/00
(Continued)

(56) References Cited

U.S. PATENT DOCUMENTS 3,906,634 A  9/1975 Aspel
3,919,772 A  11/1975 Lenczycki
(Continued)

FOREIGN PATENT DOCUMENTS

DE  10029256 A1  11/2000
WO  WO-1994026200 A1  11/1994
(Continued)

OTHER PUBLICATIONS

"U.S. Appl. No. 14/805,977, Corrected Notice of Allowance dated Nov. 14, 2017", 5 pgs.
(Continued)

*Primary Examiner* — Matthew M Nelson
(74) *Attorney, Agent, or Firm* — Schwegman Lundberg & Woessner, P.A.

(57) ABSTRACT

Methods of selecting or designing an implant to be used in a patient are provided. A CT scan of a patient's mouth is performed. A 3D CAD model of the patient's mouth is created utilizing data generated by the CT scan. Properties of the patient's mouth are determined based upon CT scan data and assigned to the 3D CAD model. A desired location for an implant is selected. A FEA simulation is performed on the 3D CAD model to choose an implant or to design an implant that optimizes a selected variable.

10 Claims, 4 Drawing Sheets

Related U.S. Application Data continuation of application No. 14/805,977, filed on Jul. 22, 2015, now Pat. No. 9,888,985, which is a continuation of application No. 13/530,708, filed on Jun. 22, 2012, now Pat. No. 9,089,380, which is a continuation of application No. 12/151,261, filed on May 5, 2008, now Pat. No. 8,206,153.

(60) Provisional application No. 60/930,812, filed on May 18, 2007.

(51) Int. Cl.
 A61B 6/14 (2006.01)
 A61B 6/00 (2006.01)
 A61B 34/10 (2016.01)
 A61C 13/00 (2006.01)
 G16H 20/40 (2018.01)

(52) U.S. Cl.
 CPC ............ *A61B 34/10* (2016.02); *A61C 8/009* (2013.01); *A61C 13/0004* (2013.01); *A61B 2034/105* (2016.02); *A61B 2034/108* (2016.02); *G16H 20/40* (2018.01)

(58) Field of Classification Search
 USPC .... 433/24, 81, 172–176, 215; 382/128, 154, 382/291; 606/86 R; 700/98; 378/4, 378/21–27
 See application file for complete search history.

(56) References Cited

U.S. PATENT DOCUMENTS

| | | |
|---|---|---|
| 3,958,471 A | 5/1976 | Muller |
| 4,011,602 A | 3/1977 | Rybicki et al. |
| 4,056,585 A | 11/1977 | Waltke |
| 4,086,701 A | 5/1978 | Kawahara et al. |
| 4,177,562 A | 12/1979 | Miller et al. |
| 4,294,544 A | 10/1981 | Altschuler et al. |
| 4,306,862 A | 12/1981 | Knox |
| 4,325,373 A | 4/1982 | Slivenko et al. |
| 4,341,312 A | 7/1982 | Scholer |
| 4,364,381 A | 12/1982 | Sher |
| 4,439,152 A | 3/1984 | Small |
| 4,543,953 A | 10/1985 | Slocum et al. |
| 4,547,157 A | 10/1985 | Driskell |
| 4,571,180 A | 2/1986 | Kulick |
| 4,611,288 A | 9/1986 | Duret et al. |
| 4,624,673 A | 11/1986 | Meyer |
| 4,663,720 A | 5/1987 | Duret et al. |
| 4,713,004 A | 12/1987 | Linkow et al. |
| 4,756,689 A | 7/1988 | Lundgren et al. |
| 4,758,161 A | 7/1988 | Niznick |
| 4,767,331 A | 8/1988 | Hoe |
| 4,772,204 A | 9/1988 | Soderberg |
| 4,795,432 A * | 1/1989 | Karczmer ............ A61M 5/3257 604/110 |
| 4,821,200 A | 4/1989 | Oberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,906,420 A | 3/1990 | Brajnovic et al. |
| 4,931,016 A | 6/1990 | Sillard |
| 4,935,635 A | 6/1990 | O'harra |
| 4,961,674 A | 10/1990 | Wang et al. |
| 4,964,770 A | 10/1990 | Steinbichler et al. |
| 4,986,753 A | 1/1991 | Sellers |
| 4,988,297 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jorneus |
| 5,071,351 A | 12/1991 | Green, Jr. et al. |
| 5,073,111 A | 12/1991 | Daftary |
| 5,087,200 A | 2/1992 | Brajnovic et al. |
| 5,100,323 A | 3/1992 | Friedman et al. |
| 5,104,318 A | 4/1992 | Piche |
| 5,106,300 A | 4/1992 | Voitik |
| 5,122,059 A | 6/1992 | Durr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jorneus |
| 5,145,372 A | 9/1992 | Daftary et al. |
| 5,176,516 A | 1/1993 | Koizumi |
| 5,188,800 A | 2/1993 | Green et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic et al. |
| 5,292,252 A | 3/1994 | Nickerson et al. |
| 5,297,963 A | 3/1994 | Dafatry |
| 5,302,125 A | 4/1994 | Kownacki et al. |
| 5,312,254 A | 5/1994 | Rosenlicht |
| 5,312,409 A | 5/1994 | McLaughlin et al. |
| 5,316,476 A | 5/1994 | Krauser |
| 5,320,529 A | 6/1994 | Pompa |
| 5,328,371 A | 7/1994 | Hund et al. |
| 5,334,024 A | 8/1994 | Niznick |
| 5,336,090 A | 8/1994 | Wilson et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,350,297 A | 9/1994 | Cohen |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter |
| 5,370,692 A | 12/1994 | Fink et al. |
| 5,372,502 A | 12/1994 | Massen et al. |
| 5,386,292 A | 1/1995 | Massen et al. |
| 5,413,481 A | 5/1995 | Goppel et al. |
| 5,417,569 A | 5/1995 | Perisse |
| 5,417,570 A | 5/1995 | Zuest et al. |
| 5,419,702 A | 5/1995 | Beaty et al. |
| 5,431,567 A | 7/1995 | Daftary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,516,288 A | 5/1996 | Sichler et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |

(56) References Cited

U.S. PATENT DOCUMENTS

| | | |
|---|---|---|
| 5,580,246 A | 12/1996 | Fried et al. |
| 5,595,703 A | 1/1997 | Swaelens et al. |
| 5,613,852 A | 3/1997 | Bavitz |
| 5,630,717 A | 5/1997 | Zuest et al. |
| 5,636,986 A | 6/1997 | Pezeshkian |
| 5,651,675 A | 7/1997 | Singer |
| 5,652,709 A | 7/1997 | Andersson et al. |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | D'urso |
| 5,743,916 A | 4/1998 | Greenberg et al. |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorio et al. |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti et al. |
| 6,217,334 B1 | 4/2001 | Hultgren |
| 6,227,859 B1 | 5/2001 | Sutter |
| 6,283,753 B1 | 9/2001 | Willoughby |
| 6,287,119 B1 | 9/2001 | Van Nifterick et al. |
| 6,296,483 B1 | 10/2001 | Champleboux |
| 6,319,000 B1 | 11/2001 | Branemark |
| 6,322,728 B1 | 11/2001 | Brodkin et al. |
| 6,382,975 B1 | 5/2002 | Poirier |
| 6,402,707 B1 | 6/2002 | Ernst |
| 6,488,503 B1 | 12/2002 | Lichkus et al. |
| 6,497,574 B1 | 12/2002 | Miller |
| 6,540,784 B2 | 4/2003 | Barlow et al. |
| 6,568,936 B2 | 5/2003 | Macdougald et al. |
| 6,575,751 B1 | 6/2003 | Lehmann et al. |
| 6,594,539 B1 | 7/2003 | Geng |
| 6,610,079 B1 | 8/2003 | Li et al. |
| 6,619,958 B2 | 9/2003 | Beaty et al. |
| 6,629,840 B2 | 10/2003 | Chishti et al. |
| 6,634,883 B2 | 10/2003 | Ranalli |
| 6,648,640 B2 | 11/2003 | Rubbert et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert et al. |
| 6,743,491 B2 | 6/2004 | Cirincione et al. |
| 6,755,652 B2 | 6/2004 | Nanni |
| 6,772,026 B2 | 8/2004 | Bradbury et al. |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman et al. |
| 6,814,575 B2 | 11/2004 | Poirier |
| 6,821,462 B2 | 11/2004 | Schulman et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jornéus et al. |
| 6,913,463 B2 | 7/2005 | Blacklock |
| 6,926,442 B2 | 8/2005 | Stöckl |
| 6,926,525 B1 | 8/2005 | Rønvig et al. |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman et al. |
| 7,112,065 B2 | 9/2006 | Kopelman et al. |
| 7,118,375 B2 | 10/2006 | Durbin et al. |
| D532,991 S | 12/2006 | Gozzi et al. |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |

(56) References Cited

U.S. PATENT DOCUMENTS

| | | |
|---|---|---|
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu et al. |
| 7,488,174 B2 | 2/2009 | Kopelman et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-ganzlin |
| 7,632,097 B2 | 12/2009 | De Clerck |
| 7,653,455 B2 | 1/2010 | Cinader, Jr. |
| 7,654,823 B2 | 2/2010 | Dadi |
| 7,655,586 B1 | 2/2010 | Brodkin et al. |
| 7,658,610 B2 | 2/2010 | Knopp |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,774,084 B2 | 8/2010 | Cinader, Jr. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-ganzlin |
| 7,824,181 B2 | 11/2010 | Sers |
| D629,908 S | 12/2010 | Jerger et al. |
| 7,855,354 B2 | 12/2010 | Eiff et al. |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,206,153 B2 | 6/2012 | Suttin et al. |
| 9,089,380 B2 | 7/2015 | Suttin et al. |
| 9,888,985 B2 | 2/2018 | Suttin |
| 2001/0008751 A1 | 7/2001 | Chishti et al. |
| 2001/0034010 A1 | 10/2001 | Macdougald et al. |
| 2002/0010568 A1 | 1/2002 | Rubbert et al. |
| 2002/0028418 A1 | 3/2002 | Farag et al. |
| 2002/0160337 A1 | 10/2002 | Klein et al. |
| 2002/0167100 A1 | 11/2002 | Moszner et al. |
| 2003/0045786 A1* | 3/2003 | Zhao .................. A61B 5/0031 600/372 |
| 2003/0130605 A1 | 7/2003 | Besek |
| 2003/0222366 A1 | 12/2003 | Stangel et al. |
| 2004/0029074 A1 | 2/2004 | Brajnovic |
| 2004/0048227 A1 | 3/2004 | Brajnovic |
| 2004/0219477 A1 | 11/2004 | Harter |
| 2004/0219479 A1 | 11/2004 | Malin |
| 2004/0219490 A1 | 11/2004 | Gartner et al. |
| 2004/0220691 A1 | 11/2004 | Hofmeister et al. |
| 2004/0243481 A1 | 12/2004 | Bradbury et al. |
| 2004/0259051 A1 | 12/2004 | Brajnovic |
| 2005/0023710 A1 | 2/2005 | Brodkin et al. |
| 2005/0056350 A1 | 3/2005 | Dolabdjian et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0170311 A1 | 8/2005 | Tardieu et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0210949 A1 | 9/2006 | Stoop |
| 2006/0263741 A1 | 11/2006 | Imgrund et al. |
| 2006/0281041 A1 | 12/2006 | Rubbert et al. |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |
| 2007/0092854 A1 | 4/2007 | Powell et al. |
| 2007/0118243 A1* | 5/2007 | Schroeder ............. A61F 2/2875 700/118 |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0269769 A1 | 11/2007 | Marchesi |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153061 A1 | 6/2008 | Marcello |
| 2008/0153065 A1 | 6/2008 | Brajnovic et al. |
| 2008/0153069 A1 | 6/2008 | Holzner et al. |
| 2008/0176189 A1 | 7/2008 | Stonisch |
| 2008/0206714 A1 | 8/2008 | Schmitt |
| 2008/0241798 A1 | 10/2008 | Holzner et al. |
| 2008/0261165 A1 | 10/2008 | Steingart et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0187393 A1 | 7/2009 | Van Lierde et al. |
| 2009/0220916 A1 | 9/2009 | Fisker et al. |
| 2009/0220917 A1 | 9/2009 | Jensen |
| 2009/0239197 A1 | 9/2009 | Brajnovic |
| 2009/0239200 A1 | 9/2009 | Brajnovic et al. |

(56) References Cited

U.S. PATENT DOCUMENTS

| | | |
|---|---|---|
| 2009/0253097 A1 | 10/2009 | Brajnovic |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0173260 A1* | 7/2010 | Sogo ............ A61C 1/084 433/75 |
| 2010/0280798 A1 | 11/2010 | Pattijn et al. |
| 2011/0008751 A1 | 1/2011 | Pettersson |
| 2011/0191081 A1 | 8/2011 | Malfliet et al. |
| 2011/0275032 A1 | 11/2011 | Tardieu et al. |
| 2012/0010740 A1 | 1/2012 | Swaelens et al. |
| 2015/0320519 A1 | 11/2015 | Suttin et al. |
| 2018/0125613 A1 | 5/2018 | Suttin et al. |

FOREIGN PATENT DOCUMENTS

| | | |
|---|---|---|
| WO | WO-1999032045 A1 | 7/1999 |
| WO | WO-2000008415 A1 | 2/2000 |
| WO | WO-2001058379 A1 | 8/2001 |
| WO | WO-2002053055 A1 | 7/2002 |
| WO | WO-2003024352 A1 | 3/2003 |
| WO | WO-2004030565 A1 | 4/2004 |
| WO | WO-2004075771 A1 | 9/2004 |
| WO | WO-2004087000 A1 | 10/2004 |
| WO | WO-2004098435 A2 | 11/2004 |
| WO | WO-2006014130 A1 | 2/2006 |
| WO | WO-2006062459 A1 | 6/2006 |
| WO | WO-2006082198 A1 | 8/2006 |
| WO | WO-2007033157 A2 | 3/2007 |
| WO | WO-2007104842 A1 | 9/2007 |
| WO | WO-2007129955 A1 | 11/2007 |
| WO | WO-2008057955 A2 | 5/2008 |
| WO | WO-2008083857 A1 | 7/2008 |

OTHER PUBLICATIONS

"U.S. Appl. No. 14/805,977, Non Final Office Action dated Mar. 21, 2017", 8 pgs.

"U.S. Appl. No. 14/805,977, Notice of Allowance dated Oct. 5, 2017", 7 pgs.

"U.S. Appl. No. 14/805,977, Preliminary Amendment filed Sep. 10, 2015", 6 pgs.

"U.S. Appl. No. 14/805,977, Response filed Jun. 21, 2017 to Non Final Office Action dated Mar. 21, 2017", 8 pgs.

"U.S. Appl. No. 15/865,608, Final Office Action dated Jan. 10, 2019", 5 pgs.

"U.S. Appl. No. 15/865,608, Non Final Office Action dated Jun. 27, 2018", 9 pgs.

"U.S. Appl. No. 15/865,608, Notice of Allowance dated Mar. 27, 2019", 8 pgs.

"U.S. Appl. No. 15/865,608, Response filed Mar. 8, 2019 to Final Office Action dated Jan. 10, 2019", 9 pgs.

"U.S. Appl. No. 15/865,608, Response filed Sep. 27, 2018 to Non Final Office Action dated Jun. 27, 2018", 11 pgs.

"Navigator™ System for CT Guided Surgery Manual", BIOMET3i Navigator™, (Oct. 2007), 1-26.

"Surgical Guide Cookbook, Drill Guides for Every Scenario", Imaterialise Medical, (Oct. 2010), 1-87.

Van Staden, R C, et al., "Step-wise Analysis of Dental Implant Insertion Process Using Finite Element Technique", Clinical Oral Implants Research, (Jul. 2006), 20 pgs.

\* cited by examiner

METHOD FOR SELECTING IMPLANT COMPONENTS

RELATED APPLICATIONS

This application is based on U.S. Provisional Application No. 60/930,812, filed May 18, 2007, hereby incorporated by reference in its entirety.

FIELD OF INVENTION

The present invention relates generally to implant systems for implants placed in bone. More particularly, the present invention relates to restoration components for dental implant systems and a computer model for selecting or developing an implant by optimizing at least one variable utilizing finite element analysis.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osscointegration process continues.

Once the osscointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is made. The impression coping may be a "pick-up" type impression coping or a "transfer" type impression coping, both known in the art. After these processes, a dental laboratory creates a prosthesis to be permanently secured to the dental implant from the impression that was made.

More recently, single stage restoration have become more common, where an implant is placed in the patients mouth and a prosthesis is placed on this implant during the same procedure. Such a procedure typically reduces the number of visits a patient must make to a clinician, however, additional complications may occur in a patient during single stage restoration if an implant lacks proper initial stability. One way to help predict initial implant stability involves using finite element analysis ("FEA") to attempt to predict effects of placing the implant into bone. These effects may include stress levels within the implant, stress levels in bone surrounding the implant, initial implant stability, torque required to seat an implant and many other factors. However, a real-time FEA simulation of the placement of an implant into bone has not been performed to date. Rather FEA simulations have only focused on the implant after it has already been placed into bone. Thus, a need exists for a method to accurately predict effects of placing an implant into bone.

SUMMARY OF THE INVENTION

According to one process, a method of selecting an implant to be used in a patient is provided that performs a CT scan of a patient's mouth. The method creates a 3D CAD model of the patient's mouth utilizing data generated by the CT scan. Properties of the patient's mouth are determined based upon data generated by the CT scan. The determined properties of the patient's mouth are assigned to the 3D CAD model. The method selects a desired location for the implant. The implant to be placed into the patient is selected. The method performs an FEA simulation of the selected implant being installed in the patient's mouth with the 3D CAD model. The method confirms the implant chosen by the act of selecting is clinically appropriate based upon the results of the FEA simulation of the 3D CAD model.

According to another process, a method of selecting an implant to be used in a patient is provided that performs a CT scan of the patient's mouth. A 3D CAD model of the patient's mouth is created utilizing data generated by the CT scan. The method determines properties of the patient's mouth based upon data generated by the CT scan. The determined properties of the patient's mouth are assigned to the 3D CAD model. The method selects a desired location for the implant. At least one variable to be optimized by a FEA simulation is assigned. The method performs an FEA simulation on the 3D CAD model to optimize the assigned variable. The method choosing the implant from a plurality of implants to use in the patient based upon results from the act of performing the FEA simulation.

According to a further process a method of designing an implant to be used in a patient is provided that performs a CT scan of the patient's mouth. The method creates a 3D CAD model of the patient's mouth utilizing data generated by the CT scan. Properties of the patient's mouth are determined based upon data generated by the CT scan. The determined properties of the patient's mouth are assigned to the 3D CAD model. The method selects a desired location for the implant. At least one variable to be optimized by a FEA simulation is assigned. The method performs a FEA simulation on the 3D CAD model to optimize the assigned variable. The implant to use in the patient is designed based upon results from the act of performing the FEA simulation.

According to yet another process, a method of verifying a FEA simulation used to select an implant is provided that creates a 3D CAD model of an actual calibration sample. Properties of the actual calibration sample are assigned to the 3D CAD model. The method performs an FEA simulation of placing the implant into the calibration sample on the 3D CAD model to generate FEA simulation data. An actual implant is placed into the actual calibration sample. The method collects measured data during the placement of the actual implant into the actual calibration sample. The measured data gathered during the act of collecting measured data is compared with the FEA simulation data generated by the act of performing the FEA simulation. The method ascertains whether the FEA simulation data accurately predicts the measured data. The method modifies FEA simulation variables if the act of ascertaining determines the FEA simulation does not accurately predict the measured data.

According to yet a further process, a method of selecting an implant to be used in a patient performs a CT scan of a region of the patient's body to contain the implant. A 3D CAD model of the region of the patient's body is created utilizing data generated by the CT scan. Properties of the region of the patient's body are determined based upon data generated by the CT scan. The method assigns the determined properties of the region of the patient's body to the 3D CAD model. A desired location for the implant is selected. The method selects the implant to be placed into the patient. An FEA simulation is performed of the selected implant being installed in the region of the patient's body with the 3D CAD model. The method confirms the implant chosen by the act of selecting is clinically appropriate based upon the results of the FEA simulation of the 3D CAD model.

Figure 1:
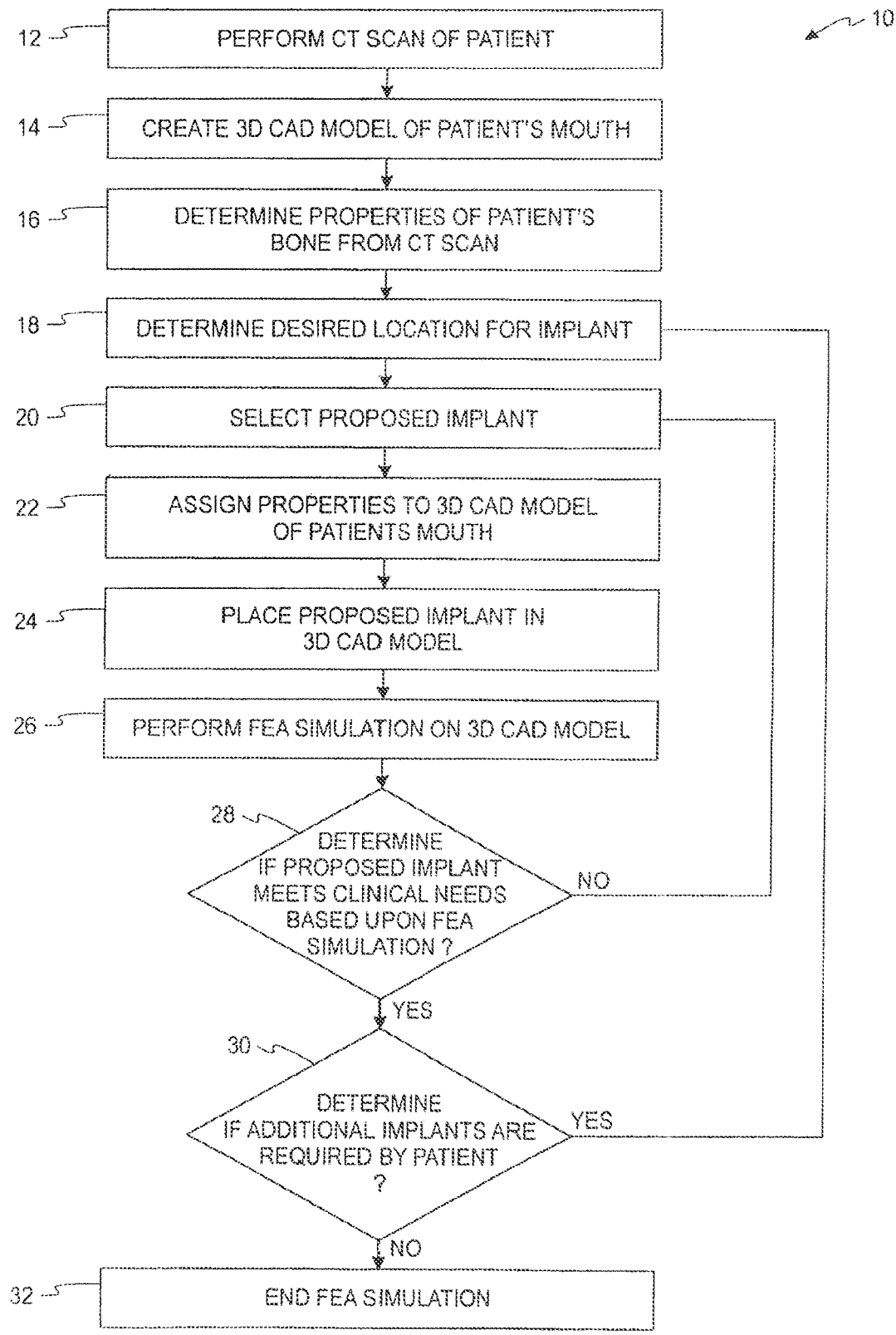
FIG. 1 is a block diagram of a method according to one process for selecting a dental implant by utilizing a Finite Element Analysis ("FEA") simulation.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

As shown in FIG. 1 a method 10 is shown to determine initial implant stability. As shown in block 12, a CT scan is performed on a patient. It is contemplated that various types of CT scans may be performed, such as Concentric CT scans or Cone-Beam CT scans. The CT scan produces data that may be used in forming a 3D CAD model of a patient's mouth within a CAD system as depicted in block 14. The CT scan allows a determination to be made regarding the type of bone found in the patient's mandible or maxilla where the implant is to be placed.

For example, the CT scan allows a practitioner to determine that Type I bone is present, a bone type that has almost all cortical bone tissue. Similarly, the CT scan may reveal that Type II, Type III, or Type IV bone is present at additional different planned implant locations. The various bone types have properties associated therewith, such as Type I bone being harder than Type IV bone. An implant being placed in Type I bone requires additional torque to seat the implant than an implant being placed in Type IV bone.

It is additionally contemplated that other technologies than CT scanning may be utilized to generate data used to form the 3D CAD model, such as ultrasonic scanning, MRI, or other scanning techniques.

Once the type, or types, of bone that implants will be placed in is determined, material properties for the bone may be assigned to the 3D CAD model of the patient's mouth, as shown in block 16.

The 3D CAD model of the patient's mouth allows a practitioner to determine locations to place the implants to be utilized, and also allows the practitioner to select particular implants to use on the patient. First, by analyzing the patient's particular anatomical structure, the practitioner determines desired locations for implants at block 18. Based on the patient's anatomical structure at the desired locations, a practitioner selects an implant to be placed within the patient at block 20. As the general ranges for material properties for Type I-Type IV bone are known, the 3D CAD model of the bones of the patient are assigned material properties at block 22. The assigning of material properties may be performed automatically by software based on the results of the CT scan, or a practitioner may analyze the CT scan and assign material properties to the 3D CAD model of the patient based on what is shown on the CT scan. Based on output from CT scan, such as the number of Hounstield's units obtained from the CT scan, a bone type may be obtained.

The CAD system contains a library of dental implants and other restorative components that a practitioner may choose from when developing a treatment plan for a patient. As shown at block 24, the practitioner selects a proposed implant to use within a first implant site of the patient within the CAD system. The CAD system contains a library of dental implants, so that 3D models exist of the various implants that a practitioner may select. The selection of a proposed implant also causes the CAD system to create an osteotomy for the selected implant at the first implant site of the 3D CAD model.

As depicted in block 26, once the practitioner has selected a proposed implant, a finite element analysis ("FEA") simulation is preformed. The FEA simulation may evaluate placing the implant into a patient's bone, the implant and bone immediately after placement of the implant, and further may analyze the implant and bone after oseointegration occurs. Thus, the FEA simulation analyzes the characteristics and conditions the implant and the bone as the implant is being placed into the bone, not just following the placement of the implant.

The FEA simulation of the implant placement analyzes the torque necessary to seat the implant into the bone. Based on the bone type present in the area around the implant site, as well as the characteristics of the implant and characteristic of the osteotomy, the amount of torque required to drive the implant into the bone is determined using the FEA simulation. After the simulation has determined the torque required to seat the implant within the bone, initial implant stability is analyzed. Knowing the amount of torque required to seat the implant is important, as using more torque than required to obtain a needed level of initial implant stability can generate more friction between the implant and the bone, which generates heat that can damage bone cells near the implant.

Initial implant stability is a measure of the stiffness of the connection between the bone and the dental implant, prior to osseointegration occurring. Initial implant stability can be used to determine how likely it is that the implant may loosen prior to osscointegration occurring. The higher the initial implant stability, the less likely the implant is to come loose. Factors that may influence initial implant stability, and that can be accounted for in the FEA simulation, include implant geometry, such as the thread design and implant size, bone type, and osteotomy properties, such as osteotomy geometry, whether the osteotomy has a counter sink, and whether the osteotomy is tapped.

Further, the FEA simulation may be used to calculate a resonant frequency of the implant and bone assembly, at the time of implantation. A resonant frequency analysis ("RFA") allows a practitioner to track the osseointegration of the implant. As the implant is integrated into the bone, the resonant frequency changes, indicating to the practitioner how osseointegration is progressing.

The FEA simulation further may be used to analyze the stress and strain generated as the implant is placed in to the osteotomy. This analysis can be used to evaluate the stress and strain at the interface of the bone and the implant, as well as the stress and strain within the patient's bone. Thus, the FEA simulation allows a practitioner to determine the potential stress and strain that will exist within the patient as the implant is placed into the bone.

Thus, the FEA simulation allows a practitioner to evaluate many factors of a selected implant in a 3D virtual environment, prior to performing any surgical procedures on a patient. Thus, a practitioner may select an implant, virtually place the implant into the 3D model of the patient's bone, and perform an FEA simulation on the implant and the bone as the implant is being placed into the 3D model of the patient's bone.

From the FEA simulation, a practitioner may determine, as shown in block 28, whether the selected implant offers necessary initial implant stability without requiring too high a level of torque being needed to place the implant into the patient's bone and without placing too much stress or strain on the bone. If the practitioner determines that the FEA simulation indicates that the selected implant meets the patient's clinical needs and offers appropriate initial implant stability without producing too much stress or strain within the bone or at the bone and implant interface, the practitioner has verified that an acceptable implant has been selected.

If the selected implant is determined to not meet the patient's clinical needs, the practitioner selects a different implant, and repeats the process as shown in blocks 20-28 until an acceptable implant is found.

Once an acceptable implant is found, as shown in block 30, it is determined if there are any additional implant locations that need to be analyzed. If there are additional implant locations, the practitioner repeats the process shown in blocks 18-28 until there are no additional implant locations.

Once every desired implant location has been analyzed and an appropriate implant for each proposed location found, the FEA simulation may be ended.

It is contemplated that the FEA simulation may allow one or more of the properties to be optimized. For example, initial implant stability may be optimized, such that the selected implant allows immediate loading in a manner that will be less likely to cause the implant to come loose prior to osseointegration. Similarly, an implant may be selected that maximizes the initial implant stability relative to a given maximum torque required to install an implant.

Figure 2:
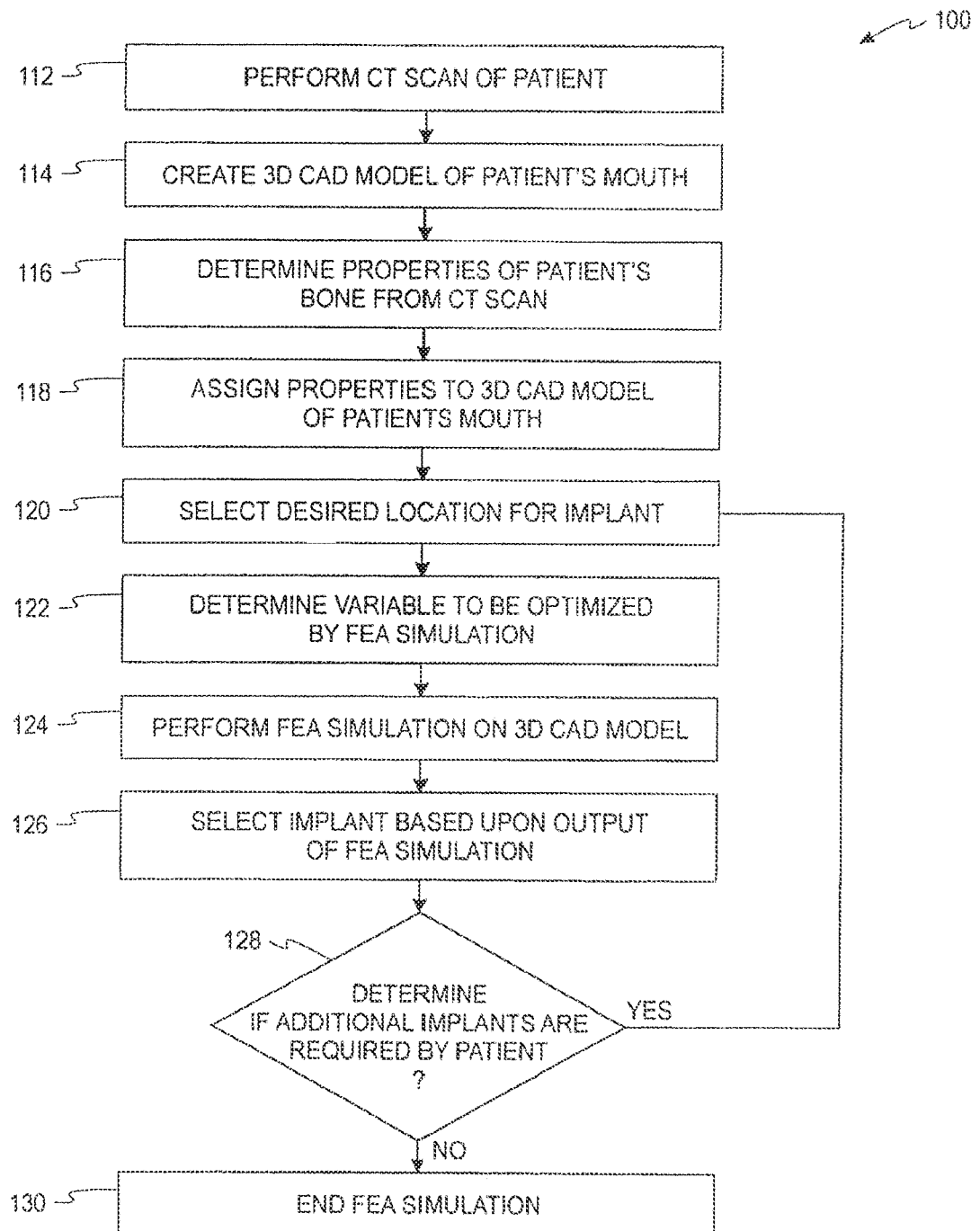
FIG. 2 is a block diagram of a method according to another process for selecting a dental implant by utilizing a FEA simulation.

Turning now to FIG. 2, a method 100 is shown that depicts a similar method to the method 10 depicted in FIG. 1, expect the method 100 of FIG. 2 uses software to optimize the implant selection based on a selected criteria or criterion.

As shown in block 112, a CT scan is performed on a patient that is used in block 114 to create a 3D CAD model of the patient's mouth. Based on the CT scan, properties of the patient's bone may be determined, as shown in block 116. It is contemplated that the properties of the patient's bone may be determined by selecting the types of bone in a patient's mouth, and assigning properties to regions of the 3D CAD model based upon typical material properties for that type of bone as shown in block 118. Alternatively, the CT scan may be used to determine bone density such that a magnitude of bone density is assigned various regions within the 3D CAD model based upon the CT scan.

Once the 3D CAD model has been assigned properties based upon the CT scan, the practitioner determines the desired locations for implant placement, as shown at block 120. Next, as shown in block 122, the practitioner determines at least one variable to optimize utilizing a FEA simulation. The variable to be optimized may be, for example, the initial implant stability, the amount of torque to install an implant, an acceptable amount of stress and strain within the bone around the implant, some other variable, or some combination of variables. An example of a combination of variables would be to optimize the initial implant stability for a low torque level required to seat an implant.

After the variable, or variables, to be optimized is selected, a FEA simulation of implant placement is performed at block 124. The FEA simulation may evaluate a plurality of implants contained in a library of the 3D CAD system. The FEA simulation produces a result at block 126 that informs a practitioner of the implant that optimizes the result for the variable, or variables, the practitioner had selected. For example, if a practitioner had chosen to maximize initial implant stability while minimizing placement torque, the FEA simulation would be performed on a variety of implants, and the FEA simulation would inform the practitioner of the particular implant that best meets the selected criterion. Once the implant for a first desired location has been selected, it is determined at block 128 if there are any additional implants required by the patient. If additional implants are required, the method returns to step 120 for the next implant. If there are no additional implants, the FEA simulation is ended, as shown in block 130.

It is contemplated according to another method that the practitioner may constrain the results given by the FEA simulation as shown in FIG. 2. For example, the practitioner may specify a diameter for the implant, and then the FEA simulation will be limited to optimizing the criterion selected only for implants of the chosen diameter. Additional examples of variable constraints the practitioner may place on the FEA simulation include, but are not limited to, implant length, implant thread design, osteotomy profile, whether the osteotomy has a countersink, and whether the osteotomy is tapped.

Figure 3:
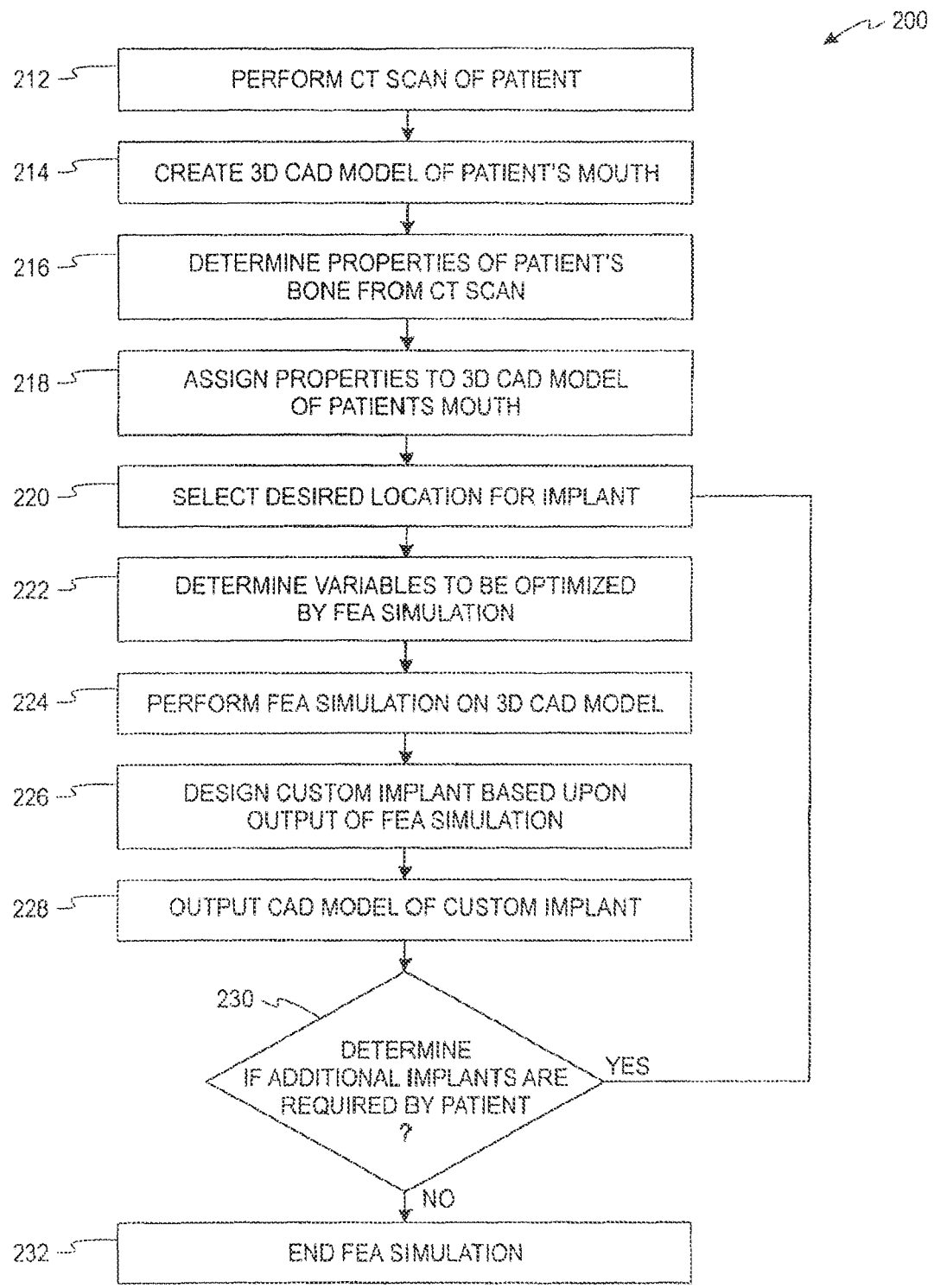
FIG. 3 is a block diagram of a method according to a further process for designing a dental implant by utilizing a FEA simulation.

As shown in FIG. 3, a further method 200 is shown in which a custom patient specific implant is designed based upon an FEA simulation. Similar to the methods previously described, a CT scan of a patient's mouth is taken at block 212. From the CT scan, a 3D CAD model of the patient's mouth is created, as depicted at block 214. As depicted at block 216, properties of the patient's bone are determined from the CT scan, such as bone type, or bone density. Once the properties of the patient's mouth are determined, the properties are assigned to 3D CAD model of the patient's mouth at block 218.

At block 220 of FIG. 3, the practitioner then selects desired locations for at least one implant. The practitioner at block 222 selects at least one variable to optimize using an FEA simulation, such as, for example, creating a high level of initial implant stability with a low level of torque required to seat the implant.

An FEA simulation is performed on the 3D CAD model to determine implant-design variables at step 224. Based upon the implant-design variables determined by the FEA simulation, a custom implant is designed for the patient that optimizes the at least one variable previously selected by the practitioner, as shown at block 226. A 3D CAD model of the custom implant is created at block 228 that may be used to machine a custom implant. The method determines at block 230 if there is an additional implant required by the patient. If there is, the method returns to block 220 if not, the FEA simulation is ended as shown at block 232.

It is contemplated according to some processes that a limited number of implant design variables may be modified to create a custom implant for a patient. Implant variables that may be modified include, but are not limited to, implant diameter, implant length, implant material, implant surface preparation, and implant thread design including thread type, thread width, diameter, and the thread pitch.

Figure 4:
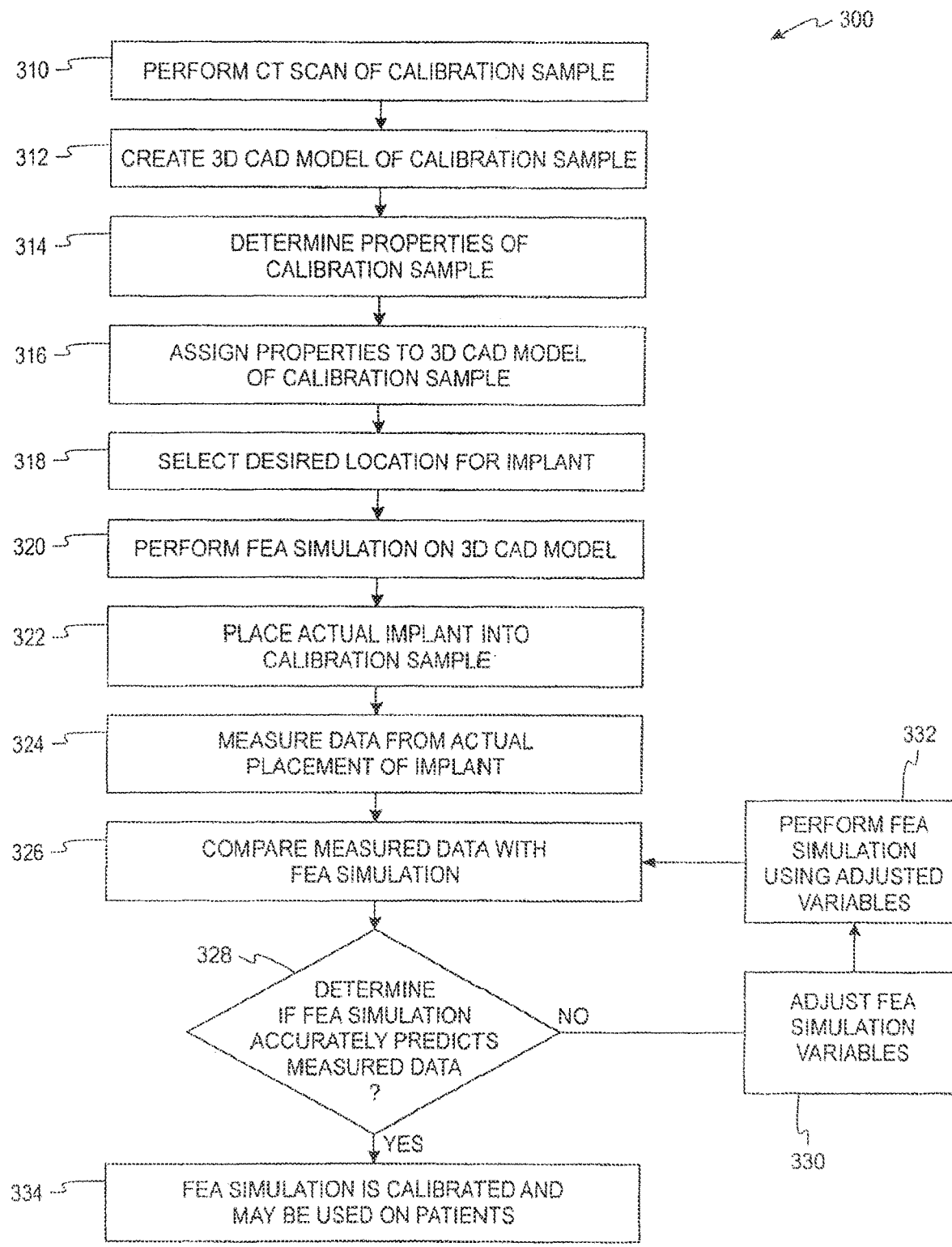
FIG. 4 is a block diagram of a method according to one process for verifying a FEA simulation.

While an FEA simulation is a valuable tool for selecting or designing a proper implant for a patient, the FEA simulation must be verified by comparing an FEA simulation with measured data collected when placing an implant into a sample, as shown by method 300 in FIG. 4. FIG. 4 illustrates the manner in which the FEA modeling analysis is verified.

As shown at block 310, a CT scan is performed on a calibration sample. Actual material properties of the calibration sample are known. Data generated by the CT scan of the calibration sample is used to form a 3D CAD model of the calibration sample at block 312. Next, properties of the calibration sample are determined at block 314 and assigned to the 3D CAD model at block 316. A desired location for placing the implant within the calibration sample is selected at block 318. Block 320 depicts a FEA simulation being performed on the 3D CAD model.

As shown at block 322, an actual implant is placed into the calibration sample. The implant is placed into the calibration sample using a test fixture that measures data during the placement of the implant into the calibration sample as shown at block 324. Examples of data that may be collected include the torque required to place the implant, the stress and strain levels of the implant, and the stress and strain level of the calibration sample near the implant. Once the measured data is obtained, the FEA simulation results are compared to the measured data, as shown at block 326. Next it is determined whether the FEA simulation result compares favorably with the measured data, as shown in block 328. If the FEA simulation does not accurately predict the measured data, FEA simulation variables are adjusted at block 330. Non-limiting examples of variables that may be adjusted include material properties, such as the modulus of elasticity of the bone, the yield strength of the bone or implant, shear strength of the bone or implant, mechanical properties, failure criteria, such as why the implant or bone failed, and failure response, such as what happened to the bone after failure. After adjusting the FEA simulation variables, the FEA simulation is performed again using the adjusted variables as shown at block 332. The adjusted FEA simulation results are then again compared with the measured data, and this process repeats until the FEA simulation results closely track the measured data. Once the FEA simulation is determined to accurately predict the measured data, the FEA simulation is considered to be properly calibrated, as shown at block 334.

Once the method 300 depicted in FIG. 4 is completed, one of the previous analysis methods shown in FIGS. 1-3 may be performed with confidence that the FEA simulation model produces results that accurately predict the forces and stresses present during the placement of the implant.

While the above methods have been described using CT scanning to generate data to form a 3D CAD model, it is contemplated that other methods may be used to gather this data. For example, an X-ray may be used in place of CT scan.

While the above embodiments have related to dental implants, it is contemplated that the above described methods may be utilized on other regions of a patient's body with other types of non-dental implants, such as orthopedic implants.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of verifying a finite element analysis (FEA) modeling, the method comprising:
   creating a 3D CAD model of a calibration sample;
   determining properties of the calibration sample;
   assigning the determined properties of the calibration sample to the 3D CAD model;
   selecting a desired location for an implant;
   performing an FEA simulation of the implant being installed in the calibration sample with the 3D CAD model;
   measure data from actual placement of the implant into the calibration sample;
   compare the measured data with the FEA simulation.

2. The method of claim 1, further including:
   performing a CT scan of the calibration material.

3. The method of claim 2, wherein the properties of the calibration sample are known properties.

4. The method of claim 1, wherein performing the FEA simulation is a real-time simulation of placing the implant into the calibration sample.

5. The method of claim 1, further including:
   installing the implant into the calibration material.

6. The method of claim 5, wherein the implant is installed into the calibration material using a test fixture that measures the data during the placement of the implant into the calibration sample.

7. The method of claim 6, wherein the data includes 1) a torque required to install the implant, 2) a stress and strain level of the implant, and 3) a stress and strain level of the calibration sample adjacent to the implant.

8. The method of claim 1, wherein comparing the measured data with the FEA simulation includes:
   determining whether the FEA simulation accurately predicts the measured data.

9. The method of claim 8, wherein; when the FEA simulation does not accurately predicts the measured data, the method includes:
   adjusting FEA simulation variables; and
   reperforming the FEA simulation with the adjusted FEA simulation variables.

10. The method of claim 8, wherein; when the FEA simulation accurately predicts the measured data, the method includes:

confirming calibration of the FEA simulation such that the FEA calibration can be used on patients.

\* \* \* \* \*

UNITED STATES PATENT AND TRADEMARK OFFICE
CERTIFICATE OF CORRECTION

PATENT NO. : 10,925,694 B2
APPLICATION NO. : 16/458984
DATED : February 23, 2021
INVENTOR(S) : Suttin et al.

Page 1 of 1

It is certified that error appears in the above-identified patent and that said Letters Patent is hereby corrected as shown below:

In the Claims

In Column 8, Line 59, in Claim 9, delete "wherein;" and insert --wherein,-- therefor In Column 8, Line 65, in Claim 10, delete "wherein;" and insert --wherein,-- therefor Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*